(12) United States Patent
Lamberton et al.

(10) Patent No.: US 9,435,770 B2
(45) Date of Patent: Sep. 6, 2016

(54) METHOD OF MAKING A FLEXIBLE DELAY LINE, A FLEXIBLE DELAY LINE AND A TRANSDUCER

(71) Applicant: GENERAL ELECTRIC COMPANY, Schenectady, NY (US)

(72) Inventors: Gary Austin Lamberton, Glenville, NY (US); Michael Rowe, Glenville, NY (US)

(73) Assignee: General Electric Company, Schenectady, NY (US)

( * ) Notice: Subject to any disclaimer, the term of this patent is extended or adjusted under 35 U.S.C. 154(b) by 599 days.

(21) Appl. No.: 13/706,559

(22) Filed: Dec. 6, 2012

(65) Prior Publication Data
US 2014/0158245 A1   Jun. 12, 2014

(51) Int. Cl.
*G01N 29/24*    (2006.01)
*G01N 29/28*    (2006.01)

(52) U.S. Cl.
CPC .......... *G01N 29/28* (2013.01); *G01N 29/2468* (2013.01)

(58) Field of Classification Search
CPC .................................................. G01N 29/28
USPC .................... 73/644, 632, 642; 310/338, 335
See application file for complete search history.

(56) References Cited

U.S. PATENT DOCUMENTS

| | | | |
|---|---|---|---|
| 3,394,586 A | 7/1968 | Cross | |
| 3,663,842 A * | 5/1972 | Miller | 310/338 |
| 4,019,373 A | 4/1977 | Freeman et al. | |
| 4,158,773 A * | 6/1979 | Novak | 250/361 R |
| 4,193,009 A * | 3/1980 | Durley, III | 310/323.19 |
| 4,435,985 A * | 3/1984 | Wickramasinghe | 73/642 |
| 4,728,844 A * | 3/1988 | Wilson et al. | 310/327 |
| 5,735,282 A | 4/1998 | Hossack | |
| 5,777,230 A * | 7/1998 | Vandervalk | 73/632 |
| 6,298,727 B1 * | 10/2001 | Fleming et al. | 73/644 |
| 6,781,287 B1 * | 8/2004 | Dam et al. | 310/334 |
| 7,367,236 B2 | 5/2008 | Georgeson et al. | |
| 7,478,569 B2 | 1/2009 | Bossi et al. | |
| 7,757,558 B2 | 7/2010 | Bossi et al. | |
| 7,975,549 B2 * | 7/2011 | Fetzer | G01N 29/2468 73/626 |
| 2006/0226738 A1 * | 10/2006 | Kurtz et al. | 310/338 |
| 2011/0032800 A1 | 2/2011 | Casula | |

* cited by examiner

*Primary Examiner* — J M Saint Surin
(74) *Attorney, Agent, or Firm* — McNees Wallace & Nurick LLC

(57) ABSTRACT

A method of making a flexible delay line for a transducer, a flexible delay line, and a transducer are provided. The method includes providing a mold having a desired geometry, applying a flexible material to the mold, curing the flexible material in the mold, and removing the cured material from the mold. The cured material forms a flexible delay line having a geometry conforming to a face of the ultrasonic transducer. The flexible delay line for a transducer includes a flexible material having an aperture shaped to receive a face of the transducer. The flexible delay line is operable to conform to a flat or an irregular surface.

18 Claims, 4 Drawing Sheets

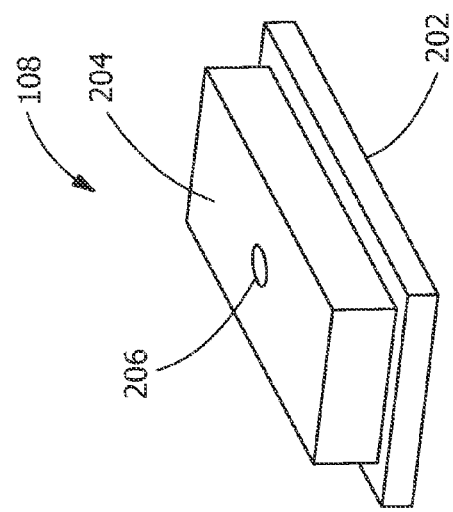
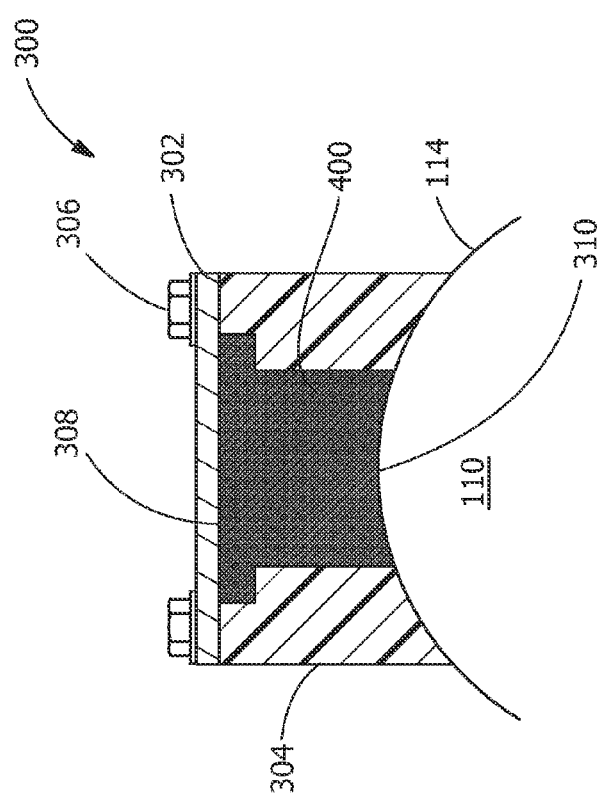
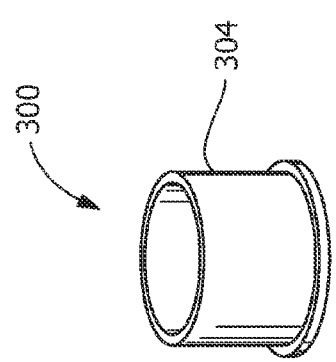

METHOD OF MAKING A FLEXIBLE DELAY LINE, A FLEXIBLE DELAY LINE AND A TRANSDUCER

FIELD OF THE INVENTION

The present invention relates generally to ultrasonic transducers and delay lines. More specifically, to a method of making a flexible delay line for an ultrasonic transducer, a flexible delay for a transducer, and a transducer that provide a flexible surface in measuring objects.

BACKGROUND OF THE INVENTION

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the power generation to inspect gas turbine engine structures for any type of internal or external damage to or defects (flaws) in the structure. Inspection may be performed during manufacturing or after the completed structure has been put into service, including field testing, to validate the continued integrity and fitness of the structure.

During NDI, one or more sensors may move over the portion of the structure to be examined, and receive data regarding the structure. Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse-echo, or mechanical impedance sensors are typically used to provide indications of voids or porosity, such as in adhesive bondlines of the structure. High resolution inspection of gas turbine structures is commonly performed using ultrasonic testing (UT) to provide an image of the part or structure under inspection. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors.

Ultrasonic transducers may include delay lines. Delay lines for ultrasonic transducers are typically made of plexiglass or similar material which is hard and must be machined to shape. NDI personnel do not typically have this capability. Lead times from manufacturers producing delay lines is oftentimes two or more weeks which is insufficient to meet NDI demands.

Therefore, a method of making a flexible delay line for an ultrasonic transducer, a flexible delay for a transducer, and a transducer that do not suffer from the above drawbacks are desirable in the art.

SUMMARY OF THE INVENTION

According to an exemplary embodiment of the present disclosure, a method of making a flexible delay line for an ultrasonic transducer is provided. The method includes providing a mold having a desired geometry. The method includes applying a flexible material to the mold. The method includes curing the flexible material in the mold. The method includes removing the cured material from the mold. The cured material forms a flexible delay line having a geometry conforming to a face of the ultrasonic transducer.

According to another exemplary embodiment of the present disclosure, a flexible delay line for a transducer is provided. The flexible delay line includes a flexible material having an aperture shaped to receive a face of the transducer. The flexible delay line is operable to conform to a flat or an irregular surface.

According to another exemplary embodiment of the present disclosure, a transducer is provided. The transducer includes a face integrated with the transducer. The transducer includes a flexible delay line for receiving the face. The flexible delay line comprises a flexible material having an aperture shaped to receive the face of the transducer. The flexible delay line is operable to conform to a flat or an irregular surface.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 2 is a perspective view of a flexible delay line of the present disclosure.

FIG. 4 is a schematic of a mold and a flexible delay line formed using the mold of the present disclosure.

FIG. 5 is a schematic of an alternative mold for making a flexible delay line of the present disclosure.

Wherever possible, the same reference numbers will be used throughout the drawings to represent the same parts.

DETAILED DESCRIPTION OF THE INVENTION

The present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein; rather, these embodiments are provided so that this disclosure will satisfy applicable legal requirements.

Provided is a method of making a flexible delay line for an ultrasonic transducer. The method includes providing a mold having a desired geometry. The method includes applying a flexible material to the mold. The method includes curing the flexible material in the mold. The method includes removing the cured material from the mold. The cured material forms the flexible delay line having a geometry conforming to the face of the ultrasonic transducer.

One advantage of an embodiment of the present disclosure includes providing a method of making a flexible delay line in the lab or field. Another advantage of an embodiment is a flexible delay line that conforms to any mold geometry provided. Yet another advantage is a flexible delay line that conforms to flat surfaces, irregular surfaces, non-uniform, or curved surfaces.

Figure 1:
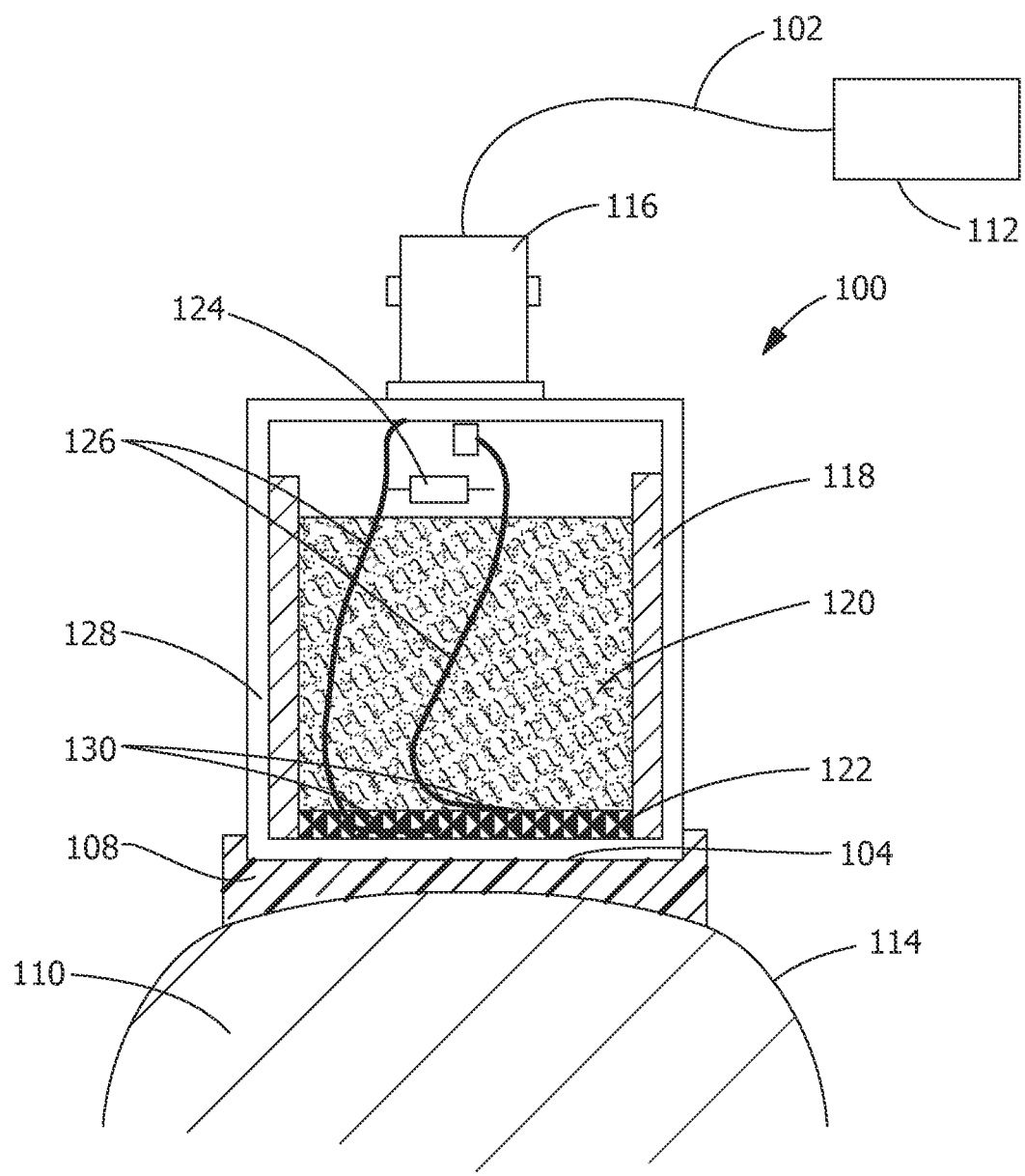
FIG. 1 is a front partial sectional illustration of a transducer of the present disclosure.

FIG. 1 is a front partial sectional illustration of a transducer 100. Transducer 100 includes an external housing 128 surrounding an inner sleeve 118. Inner sleeve 118 surrounds backing 120 and active element 122. Active element 122 is electrically connected to electrodes 130 which are connected to electrical leads 126 and electrical network 124. Electrical network 124 is connected to connector 116 which communicates with control 112 by a connection 102. Control 112 receives and processes singles from face 104 or wear plate during testing. As shown in FIG. 1, face 104 is surrounded by flexible delay line 108. In another embodiment, face 104 includes a sheath for holding flexible delay line 108. As utilized herein, "delay line" is a structure that improves near surface resolution for inspection or shifts the focus of the transducer to an area of interest for inspection. Delay line moves transition to face interface enables better near face inspection. In an alternative embodiment, flexible delay line 108 is attached directly to face 104. Flexible delay line 108 includes a flexible material having an aperture for receiving face 104 of transducer 100. Flexible delay line 108 is operable to conform to flat surfaces, irregular surfaces, non-uniform surfaces or curved surfaces. As shown in FIG. 1, flexible delay line 108 conforms to curved surface 114 of component 110.

Transducer 100 may be used to non-destructively inspect any number of components 110 in a variety of industries where detection of flaws or defects in component 100 is required, such as in the aircraft, automotive, marine, or construction industries.

The term "component" 110 is not meant to be limiting, as transducer 100 may be used to inspect any number of parts or structures of different shapes and sizes, such as machined forgings, castings, pipes, or composite panels or parts. The inspection could be performed on newly manufactured components or existing components or structures that are being inspected for preventative maintenance purposes. Component 110 may include any number of materials. For example, component 110 may be a metallic material, such as, but not limited to, aluminum or steel, or a composite material, such as, but not limited to, carbon-reinforced polymer.

As shown in FIG. 2, a schematic of flexible delay line 108 is provided. Flexible delay line 108 is constructed using molds 300 (see FIG. 3). Flexible delay line 108 includes first surface 202 for interfacing with surface 114 of component 110. Flexible delay line 108 includes second surface 204 for interfacing with face 104 of transducer 100. In one embodiment, flexible delay line 108 includes aperture 206 or slot for receiving face 104 of transducer 100. Although shown as generally circular in FIG. 2, aperture 206 shape is generally similar to face 104 shape of transducer 100, and may include any shape that is similar to face 104. In an alternative embodiment, flexible delay line 108 does not include aperture 206. Suitable examples of flexible material 400 for flexible delay line 108 include, but are not limited to, rapid curing two-part silicone rubbers, such as, but not limited to, REPLISET® materials, RepliSet-F5, RepliSet-F1, RepliSet-T3, RepliSet-T1, RepliSet-GF1, and RepliSet-GT1, available from Struers, Inc. (Westlake, Ohio), rapid curing two-part siloxane-silicone rubbers, such as but not limited to, MICROSET materials, Microset 100, Microset 101SS, Microset 101FF, Microset 101TH, Microset 101FR, Microset 101XF, Microset 101FS, available from Isomark LTD (Warwickshire, United Kingdom). Flexible delay line 108 allows for transmission of sound in the range of between about 60 decibels (dB) to about 80 dB. Thickness of flexible delay line 108 varies but is generally between about 12.7 millimeters (about 0.5 inches) to about 101.6 millimeters (about 4.0 inches), or alternatively between about 20 millimeters to about 90 millimeters, or alternatively between about 30 millimeters to about 85 millimeters.

Figure 3:
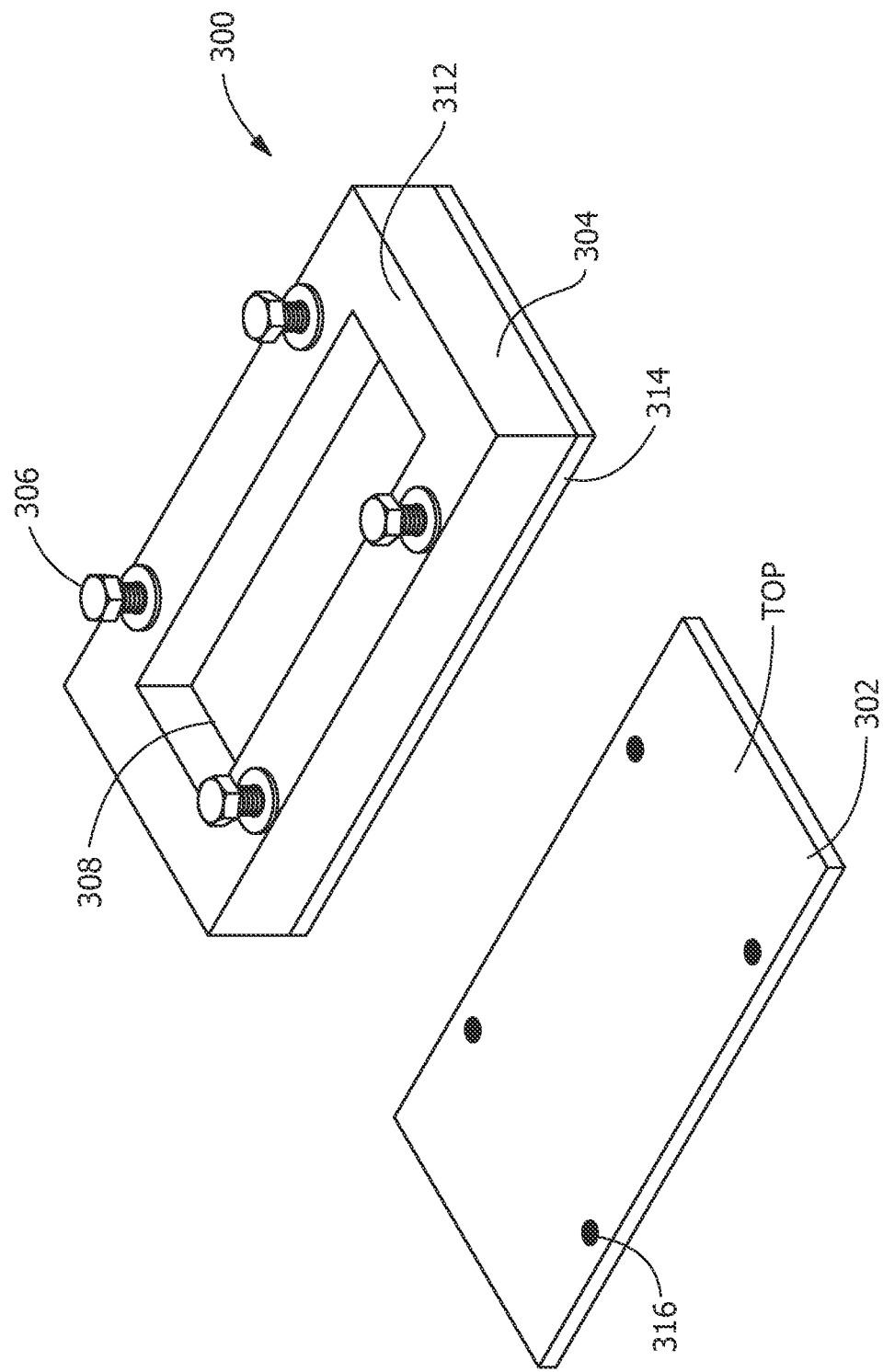
FIG. 3 is a schematic of a mold for making a flexible delay line of the present disclosure.

As shown in FIG. 3, mold 300 for forming flexible delay line 108 is provided. Mold 300 includes a body 304 for receiving uncured flexible material 400 (see FIG. 4) to form flexible delay line 108. Mold 300 includes first opening 308 and second opening 310 both adapted to receive flexible material 400 (see FIG. 4). Second opening 310 provides area for mold 300 and flexible material therein to conform to surface 114 of component 100 or any desired shape or template for flexible delay line 108. Mold includes cover 302 for use during curing of flexible material 400 to form flexible delay line 108. Cover 302 includes apertures 316 for receiving attachment members 306 to secure cover to mold body 304. Suitable attachment members 306, include, but are not limited to, hooks, screws, bolts, nails, and combinations thereof. Mold 300 includes any shape for body 304, such as the rectangular shape show in FIG. 3 or a circular shape as shown in FIG. 5. Body 304 of mold 300 is constructed from any suitable material, depending on surface 114 of component 110. In one embodiment, body 304 of mold 300 is constructed from flexible materials that conform to surface 114 of component, suitable examples include, but are not limited to, flexible polymers, such as, but not limited to, plastics and silicone rubbers. In an alternative embodiment, body 304 of mold 300 is constructed more rigid plastic or metal materials, such as but not limited to, DELRIN® available from DuPont Engineering Polymers (Wilmington, Del.).

FIG. 4 is a sectional view of mold 300 including flexible material 400. As illustrated, flexible material 400 is contained within mold 300 and second opening 310 allows flexible material 400 to contact surface 114 of component 110 to provide flexible delay line 108 having desired geometry that conforms to surface 114 of component 110. Mold 300 including flexible material 400 is cured to form flexible delay line 108. In one embodiment, flexible material 400 and mold 300 are cured under vacuum to prevent formation of air bubbles in flexible delay line 108. In an alternative embodiment, flexible material 400 is allowed to cure at ambient temperature for a period of about 3 to about 12 hours.

Figure 6:
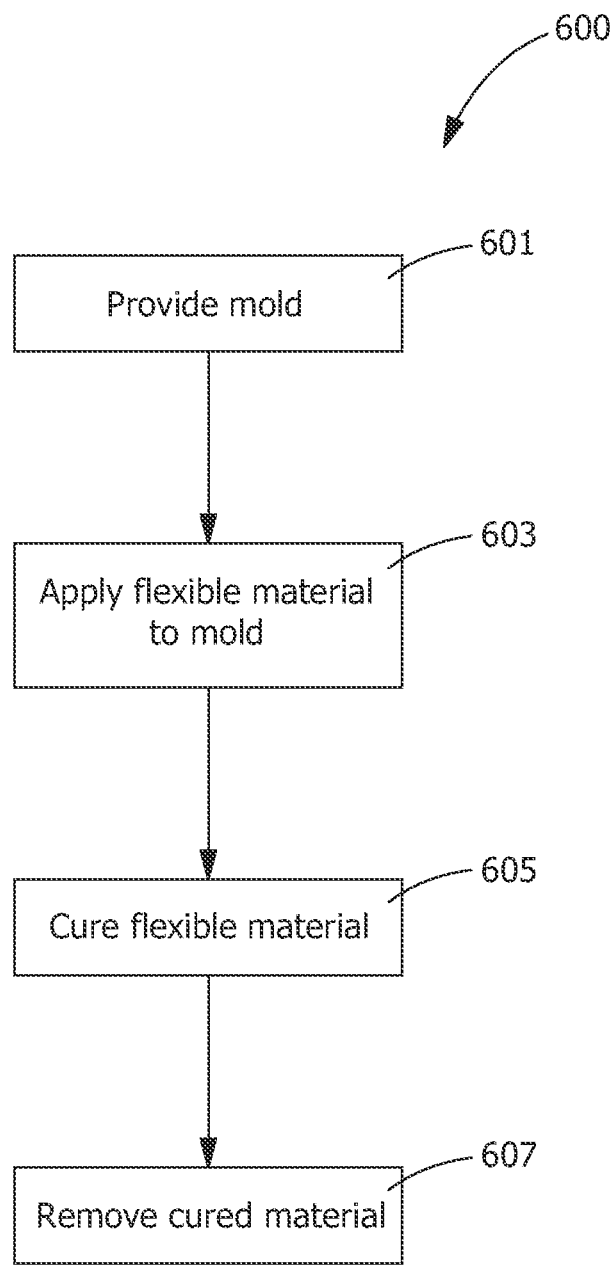
FIG. 6 is a flow chart of an exemplary method of forming a flexible delay line of the present disclosure.

FIG. 6 is a flow chart describing a method 600 of forming flexible delay line 108. Method 600 includes providing mold 300 having a desired geometry, step 601 (see FIG. 3). Method 600 may include placing one opening of mold 300, in one embodiment, second opening 310, adjacent to surface 110 of component 114 to be measured or tested. Surface 110 of component 114 may include flat surfaces, irregular surfaces, or curved surfaces. Mold 300 being made from a flexible material conforms to surface 110 of component. Method 600 includes applying a flexible material to the mold, step 603. In one embodiment, flexible material is applied to mold 300 and adjacent to surface 114 of component 110 to conform to surface 114. Method 600 includes curing the flexible material in mold 300, step 605. Method 600 includes removing the cured material from mold 300, step 607 (see FIG. 4). In one embodiment curing, step 607, is conducted under vacuum. The cured material forms flexible delay line 108 having a geometry conforming to face 104 of ultrasonic transducer 100, see FIG. 1. In one embodiment, the desired geometry of mold 300 is substantially the same shape as face 104 of transducer 100. Mold 300 is generally constructed from a flexible material 400.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of making a flexible delay line for an ultrasonic transducer having a face comprising:
    providing a mold having a desired geometry;
    applying a flexible material to the mold;
    curing the flexible material in the mold; and
    removing the cured material from the mold,
    wherein the cured material forms the flexible delay line having a geometry conforming to the face of the ultrasonic transducer, the flexible delay line having an aperture shaped to receive and surround the face of the ultrasonic transducer with the face of the ultrasonic transducer directly attached to the flexible delay line, the flexible delay line being operable to conform to a flat or an irregular surface.

2. The method of claim 1, wherein the step of curing is conducted under vacuum.

3. The method of claim 1, wherein the desired geometry of the mold is the same shape as a face of the transducer.

4. The method of claim 1, wherein the mold is flexible.

5. The method of claim 4, wherein the mold has two opposing openings for receiving the flexible material.

6. The method of claim 5, wherein the step of providing the mold includes placing one opening of the mold adjacent to a surface of a component to be inspected, the surface having a curvature.

7. The method of claim 6, wherein the flexible material is applied to the component in the flexible mold and adjacent to the surface of the component.

8. The method of claim 1, wherein the thickness of the flexible delay line is about 12.7 millimeters to about 101.6 millimeters.

9. The method of claim 1, wherein the flexible material is selected from the group consisting of a rapid curing two-part rubber-silicone and a rapid curing two-part rubber-siloxane-silicone.

10. The method of claim 1, wherein the step of curing is less than 8 hours.

11. A flexible delay line for a transducer comprising a flexible material having an aperture shaped to receive and surround a face of the transducer with the face of the transducer directly attached to the flexible delay line, wherein the flexible delay line is operable to conform to a flat or an irregular surface.

12. The flexible delay line of claim 11, wherein the irregular surface includes surfaces having curvatures, gaps, mismatches, or combinations thereof.

13. The flexible delay line of claim 11, wherein the flexible material is selected from a rapid curing two-part rubber-silicone and a rapid curing two-part rubber-siloxane-silicone.

14. The flexible delay line of claim 11, wherein the flexible delay line has a thickness of about 0.5 inches to about 4 inches.

15. A transducer comprising:
    a face integrated with the transducer; and
    a flexible delay line for receiving the face, wherein the flexible delay line comprises a flexible material having an aperture shaped to receive and surround the face of the transducer with the face of the transducer directly attached to the flexible delay line, wherein the flexible delay line is operable to conform to a flat or an irregular surface.

16. The transducer of claim 15, wherein the flexible material is selected from the group consisting of a rapid curing two-part rubber-silicone and a rapid curing two-part rubber-siloxane-silicone.

17. The transducer of claim 15, wherein the flexible delay line has a thickness of about 0.5 inches to about 4 inches.

18. The transducer of claim 15, wherein the irregular surface includes surfaces having curvatures, gaps, mismatches, or combinations thereof.

* * * * *